(12) United States Patent
Thirstrup et al.

(10) Patent No.: US 6,706,476 B1
(45) Date of Patent: Mar. 16, 2004

(54) PROCESS FOR AMPLIFYING AND LABELING SINGLE STRANDED CDNA BY 5' LIGATED ADAPTOR MEDIATED AMPLIFICATION

(75) Inventors: Kenneth Thirstrup, Copenhagen (DK); Peter Warthoe, Copenhagen (DK); Niels Bo Pettersson, Copenhagen (DK)

(73) Assignee: Azign Bioscience A/S, Copenhagen (DK)

( * ) Notice: Subject to any disclaimer, the term of this patent is extended or adjusted under 35 U.S.C. 154(b) by 17 days.

(21) Appl. No.: 09/803,263

(22) Filed: Mar. 9, 2001

Related U.S. Application Data

(60) Provisional application No. 60/226,954, filed on Aug. 22, 2000.

(51) Int. Cl.[7] .......................... C12Q 1/68; C12P 19/34; C07H 21/04
(52) U.S. Cl. ................. 435/6; 435/91.2; 435/91.52; 536/24.32; 536/24.33; 536/25.32
(58) Field of Search .............................. 435/91.1, 91.2, 435/6, 7.1, 15, 91.52, 24.3, 24.2; 536/24.3, 25.32; 935/77, 78

(56) References Cited

FOREIGN PATENT DOCUMENTS

WO  98/51789  * 11/1998

OTHER PUBLICATIONS

RQST00000058293 Dis/Old Clontech Prod's, Clontech Laboratories, Inc.*

* cited by examiner

*Primary Examiner*—Jeffrey Fredman
*Assistant Examiner*—Cynthia Wilder
(74) *Attorney, Agent, or Firm*—Frommer Lawrence & Haug; Thomas J. Kowalski

(57) ABSTRACT

This invention relates to a method wherein special adaptors and primers are used for single stranded cDNA amplification. The method comprises contacting RNA with an anchored cDNA synthesis primer which can anneal to RNA, a suitable enzyme which possesses reverse transcriptase activity, and a special designed adaptor which can efficiently be ligated to the 3' end of single stranded cDNA by T4 DNA ligase. Processes are provided for using specific primers annealing to the adaptors in the 5' and 3'-end of the single stranded cDNA for PCR amplifying the cDNA. The invention describes the use of this approach for generation of probes starting from low amounts of RNA to be used e.g. in hybridization towards micro-arrays.

24 Claims, 6 Drawing Sheets

(3 of 6 Drawing Sheet(s) Filed in Color)

Figure 2.

1) 5'-RNA RNA RNA RNA RNA RNA RNA RNA RNA AAA AAA AAA AAA AAA AA A
   [TTT TTT TTT TTT TTT TT T]-5'
   $T_n$ $V_{n1}$

2) NNN NNN NNN NNN NNV TTT TTT TTT TTT TTT TTT TT TAG GAC GCA ACA ATG GTC ACG-5'
   $COM_1$

3) X-[A GCG ATG AGT CCT GAC GGC TCT] [CGT AGA CTG CGT ACG]-P NNN N NN NNN NNN NNV [NNN N II III III I]-X
   $COM_3$ $COM_2$ $N_{n2}$ $Z_m$
   5' [GCA TCT GAC GCA TGC]
   $COM_4$

4) X-A GCG ATG AGT CCT GAC GGC TCT CGT AGA CTG CGT ACG NNN NNN NNN NNN NNV TTT TTT TTT TTT TTT TTT TT TAG GAC GCA ACA ATG GTC ACG-5'
   5' GCA TCT GAC GCA TGC

5) X-A GCG ATG AGT CCT GAC GGC TCT CGT AGA CTG CGT ACG NNN NNN NNN NNN NNV TTT TTT TTT TTT TTT TTT TT TAG GAC GCA ACA ATG GTC ACG-5'

6) X-A GCG ATG AGT CCT GAC GGC TCT CGT AGA CTG CGT ACG NNN NNN NNN NNN NNV TTT TTT TTT TTT TTT TTT TT TAG GAC GCA ACA ATG GTC ACG-5'
   5'-[T CGC TAC TCA GGA CTG CC]→
      Primer#1

7) X-A GCG ATG AGT CCT GAC GGC TCT CGT AGA CTG CGT ACG NNN NNN NNN NNN NNV TTT TTT TTT TTT TTT TTT TT TAG GAC GCA ACA ATG GTC ACG-5'
   5'-T CGC TAC TCA GGA CTG CCG AGA GCA TCT GAC GCA TGC NNN NNN NNN NNN NNN AAA AAA AAA AAA AAA AA ATC CTG CGT TGT TAC CTG TGC
                                                                                                                        RNA

8) X-A GCG ATG AGT CCT GAC GGC TCT CGT AGA CTG CGT ACG NNN NNN NNN NNN NNV TTT TTT TTT TTT TTT TTT TT TAG GAC GCA ACA ATG GTC ACG-5'
   5'-[T CGC TAC TCA GGA CTG CC]→
      Primer#1

9) 5'-T CGC TAC TCA GGA CTG CCG AGA GCA TCT GAC GCA TGC NNN NNN NNN NNN NNN AAA AAA AAA AAA AAA AA ATC CTG CGT TGT TAC CTG TGC
                                                                                                  ← [G GAC GCA ACA ATG GTC ACG]-5'
                                                                                                     Primer#2

US 6,706,476 B1

PROCESS FOR AMPLIFYING AND LABELING SINGLE STRANDED CDNA BY 5' LIGATED ADAPTOR MEDIATED AMPLIFICATION

RELATED APPLICATIONS/PRODUCTS & INCORPORATION BY REFERENCE

This application claims priority from U.S. application Ser. No. 60/226,954, filed Aug. 22, 2000. Reference is made to: U.S. application Ser. No. 08/871;030, filed May 18, 1998; allowed U.S. application Ser. No. 09/068,860, filed May 19, 1998; Danish application 1999 00897, filed Jun. 25, 1999; Warthoe, "A Method For Improved Reverse Transcription At High Temperature," allowed U.S. application Ser. No. 09/603,185, filed Jun. 26, 2000 (claiming priority from Danish application 1999 00897); Display Systems Biotech arrayTRACKER Low-RNA MICROARRAY PROBE (press release of Mar. 9, 2000 released Mar. 10, 2000; marketing information; and Kit Manual version 1.1, catalog #491-100). Each of these applications and/or patents and/or product literature and each document cited or referenced in each of these applications and/or patents and/or product literature, including during any prosecution ("application cited documents"), and each document cited or referenced in each of the application cited documents, and each product data sheet for each commercially available product mentioned in each of the application cited documents, are hereby incorporated herein by reference. In addition, each document cited in this text ("herein cited documents") and each document cited or referenced in each of the herein cited documents, and each product data sheet for each commercially available product mentioned herein, are hereby incorporated herein by reference. Furthermore, the inventors herein hereby confirm that the inventive entity of each of the aforementioned applications and/or patents is not "another" as to the present inventive entity, and vice versa. Even further still, the inventors herein hereby confirm that: the Display Systems Biotech arrayTRACKER Low-RNA MICROARRAY PROBE (press release of Mar. 9, 2000 released Mar. 10, 2000; marketing information; and Kit Manual version 1.1, catalog #491-100) is by the assignee of the present application; the Display Systems Biotech arrayTRACKER Low-RNA MICROARRAY PROBE (press release of Mar. 9, 2000 released Mar. 10, 2000; marketing information; and Kit Manual version 1.1, catalog #491-100) was not "on sale" or in public use in the U.S., or otherwise disclosed in a printed publication or patented in the U.S. or a foreign country, or otherwise available, more than one year prior to the effective U.S. filing date of this application, and, that Display Systems Biotech arrayTRACKER Low-RNA MICROARRAY PROBE (press release of Mar. 9, 2000 released Mar. 10, 2000; marketing information; and Kit Manual version 1.1, catalog #491-100) are embodiments of the herein invention and are by the herein inventors such that the Display Systems Biotech arrayTRACKER Low-RNA MICROARRAY PROBE (press release of Mar. 9, 2000 released Mar. 10, 2000; marketing information; and Kit Manual version 1.1, catalog #491-100) is not by "another" or "others" as to the present inventors and their assignee. Thus, the Display Systems Biotech arrayTRACKER Low-RNA MICROARRAY PROBE (press release of Mar. 9, 2000 released Mar. 10, 2000; marketing information; and Kit Manual version 1.1, catalog #491-100) is not prior art as to the present invention.

FIELD OF THE INVENTION

The present invention relates to an improved method for producing amplified heterogeneous populations of cDNA from limited quantities of RNA or other nucleic acids.

BACKGROUND OF THE INVENTION

Selective amplification of cDNAs represents a major research goal for molecular biology, with particular importance in diagnostic and forensic applications, as well as in general manipulation of genetic material.

In many important areas of research, such as in studying gene regulation in complex biological systems (e.g., the brain) having multiple phenotypes, the obtaining of an sufficient amount of RNA for isolating, cloning, and characterizing of specific regulated transcripts is problematic. Research has been hindered by, e.g., the high complexity of the mRNA, the relatively low abundance of many expressed messages, and the spatially limited expression of these messages. In particular, the isolation of sufficient RNA for micro-array analysis has been a challenge. Various labeling techniques have been developed for that purpose. These technologies can be divided into PCR and non-PCR based labeling technologies. Two of the non-PCR based methods are from NEN life science and Genisphere respectively and are based on a principle in which the detectable signal is amplified after the final hybridization.

For instance, NEN life science has developed a technology which is based on their Tyramide Signal Amplification™ (TSA) system, U.S. Pat. No. 5,196,306, which was originally developed for immunohistochemistry but has recently been adapted for micro-array analysis. Furthermore, the company Genisphere has developed their so called "Dendrimer technology" which is based on a labeled complex DNA structure which hybridizes to a target sequence. Both of these technologies have very complex protocols which require additional steps after the final hybridization of the probe to the target sequence.

Affymetrix has developed a method where the RNA is amplified prior to the labelling of the probe. This is accomplished by including a T7 promoter region into the oligo(dT) primer and using T7 RNA polymerase to generate multiple RNA copies by reverse transcribing the double stranded cDNA, U.S. Pat. No. 5,545,522.

In order to simplify the method and to be able to detect RNA at such low levels as in the sub-microgram range, the use of PCR in the amplification of the probe signal is needed. The polymerase chain reaction (PCR) is an extremely powerful technique for amplifying a specific nucleic acid. The use of PCR in gel based gene profiling technologies was introduced several years ago with the invention of the Differential Display technologies and their like (Liang & Pardee, 1992). Recently, a differential display approach has been developed to synthesize very sensitive micro-array probes (Trenkle et al., 1999). This method, however, is limited as it only amplifies about 5% of the RNA population at a time and furthermore is susceptible to the same problems of reproducibility as seen in the differential display method.

One of the demands of PCR is typically that the 5' terminus and 3' terminus sequence information is known for the synthesis of the primers. Homopolymeric tailing of the 3' terminus (Frohman et al., 1988) and the synthesis of highly degenerate nucleotide primers (Gould et al., 1989) have been implemented to improve the range of cDNAs that can be amplified and cloned with PCR.

A number of techniques have been developed to add a sequence tag to the 5'-end of single stranded cDNA. For instance, the so called 'Ligation-anchored PCR' (Troutt et al., 1992) was developed in 1992 for that purpose. It makes use of T4 RNA ligase for the ligation of a single stranded oligo to the 5'-end of a single stranded cDNA template. The use of T4 RNA ligase in ligation of single stranded templates has however never been widely used due to the low efficiency of single stranded ligations compared to ligations using e.g. T4 DNA ligase. In another example the widely used PCR synthesis kit (Clontech laboratories) is adapted from a technique developed by Chenchik et al. (U.S. Pat. No. 5,962,277). This technique makes use of the terminal transferase activity of the MMLV reverse transcriptase. By use of a special oligonucleotide it is possible for the reverse transcriptase to switch template and extend the first strand synthesis into a specific sequence. However, only full length cDNAs will be tailed with the specific sequence anchor and only sequences which have been tailed by terminal transferase activity of the reverse transcriptase will be extended. In a more recent article, the ligation of a fluorescent labeled primer toward an unlabeled 5'-phosporylated primer was efficiently carried out using T4 DNA ligase and a so called bridging primer (Jang & Steffens, 1997). This method describes the ligation of small fluorescently labeled oligonucleotides with known sequences but is not applicable for adding sequence tags to the 5'-end of e.g. cDNAs of unknown sequences.

In spite of such recent advances, including PCR and its various modifications noted above, there is a need for irmproved methods for amplifying RNA for cloning and micro-array experiments. Especially a method is sought for that is simple and reproducible and that is able to amplify limited amount of cDNA starting from heterogeneous populations of RNA.

SUMMARY OF THE INVENTION

The present invention provides novel processes for nucleic acid amplification, especially suitable for amplification of low abundant cDNA originating from a source only containing the mRNA of interest in a very limited amount.

The present invention describes a method in which a specially designed adaptor with a non-specific overhang can be efficiently ligated directly to a single stranded cDNA and amplified directly in a subsequent PCR reaction. This method is especially suitable for generating labeled probes to be used in micro array hybridization experiments when only limited amounts of RNA is available.

The overall methodologies will be capable of amplifying a broad range of messenger RNAs without prior cloning into vectors and in some instances without knowledge of the sequence. This is achieved by performing a first strand synthesis of cDNA from mRNA, using a cDNA synthesis primer containing a polythymidylate region and an anchor region, said anchor region having a pre-defined nucleotide sequence ($COM_1$) complementary to an amplification primer (primer #2). The pre-defined nucleotide sequence can be any desired nucleotide sequence, e.g., gene of interest or portion thereof of interest or gene fragment of interest.

Hereafter, a specially designed adaptor fragment is ligated to the first strand cDNA. Said adaptor is easily ligated to the cDNA via a non-specific overhang comprising non selective bases like deoxyinosines, which will keep the annealing temperature of the adaptor constant and also ensure a high equilibrium toward the specific single cDNA during the ligation. Furthermore, the adaptor contains a pre-defined nucleotide sequence ($COM_3$) complementary to an amplification primer (primer #1). The single stranded cDNA product with ligated adaptor can hereafter be subjected to standard nucleic acid amplification procedures, e.g. PCR, using two primers (primer #1 and primer #2) which are preferably single stranded nucleotides of sufficient length to act on the cDNA template for synthesis of extension products under suitable conditions.

This method of nucleic acid amplification can for example be applied in a process for detecting expression of a gene in a pre-selected cell population wherein mRNA from said cell population is amplified according to the invention thereby determining the presence or absence of mRNA corresponding to the gene of interest or portion thereof of interest or gene fragment of interest. The cell population may e.g. be from a human tissue samples, such as from brain tissue. The cell population may e.g., be from an embryonic or fetal tissue. The cell population may be only a single cell, or be comprised by up to 100 to 1,000,000 cells or even more as desired. The cell(s) can be from any desired source.

In another embodiment, the present invention comprises a process for producing a subtractive hybridization probe.

Additionally, the present invention comprises methods for making cDNA libraries from a collection of mRNA molecules.

Importantly, the present invention can be readily provided in kit form for a variety of uses. In addition to instructions, a kit will typically comprise containers of reverse transcriptase, RNA polymerase, and nucleotides which may be labeled, such as with radioactive labels (e.g. $^{14}C$, $^{3}H$, $^{32}P$, Cy3, Cy5, $^{33}P$, $^{35}S$, $^{125}I$, fluorophores, fluorescein, rhodamin and Texas Red, and the like).

DETAILED DESCRIPTION

In the present invention, a method is provided for the amplification of broad classes of cDNAs. This method involves the ligation of an adaptor into the 3'-end of a single stranded first strand cDNA molecule and subsequent nucleic acid amplification as shown in FIGS. 1 and 2 and described in detail in the steps below:

a) annealing a cDNA synthesis primer of the general formula I

$$5'\text{-}COM_1T_nV_{n1}\text{-}3' \qquad\qquad I$$

to an RNA molecule and synthesizing a first cDNA strand to form an RNA-cDNA intermediate, $COM_1$ being a pre-selected nucleotide sequence is larger than or equal to 0, preferably between 0 and 40 nucleotides long, n and no are integers each characterized as $0 \leq n$ and $n1=0$ or $n1=1$ b) separating the cDNA strand from the RNA, c) purifying the cDNA by removing the cDNA synthesis primer, d) contacting said cDNA with an adaptor, said adaptor consisting of two oligonucleotides hybridized to each other having the general formula II and III respectively

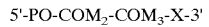

$$5'\text{-}PO\text{-}COM_2\text{-}COM_3\text{-}X\text{-}3' \qquad\qquad II$$

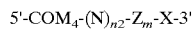

$$5'\text{-}COM_4\text{-}(N)_{n2}\text{-}Z_m\text{-}X\text{-}3' \qquad\qquad III$$

e) ligating the adaptor via the 5'-phosphate group on strand II of the adaptor to the single stranded cDNA using a DNA ligase, f) amplifying said ligated single stranded cDNA fragment obtained in step e) in a molecular amplification procedure so as to obtain amplified cDNA fragments, wherein is used at least one set of amplification primers being partly or fully complementary to the general formula II and the pre-selected nucleotide sequence ($COM_1$) of the cDNA synthesis primer respectively.

The COM$_2$ and COM$_4$ sequences of formula II and III are complementary to each other and are therefore able to form the following complex:

In formulas I, II and III COM$_1$, COM$_2$, COM$_3$ and COM$_4$ represent predefined nucleotide sequences and the number of nucleotides of the COM-sequences is an integer. COM$_1$ is larger than or equal to 0 (0≤COM$_1$), e.g., at least 1 or 3, preferably between 0 or 1 or 3 and 40 nucleotides (0≤COM$_1$≤40 or 1≤COM$_1$≤40 or 3≤COM$_1$≤40), COM$_2$ and COM$_4$ are of equal length and are larger than or equal to 4 (4≤COM$_2$, 4≤COM$_4$), preferably between 6 and 25 nucleotides (6≤COM$_2$≤25, 6≤COM$_4$≤25), COM$_3$ is larger than or equal to 0 (0≤COM$_3$), preferably between 0 and 40 nucleotides (0≤COM$_3$≤40). T is the nucleotide thymidine; V is a nucleotide selected from the group consisting of A, G and C; PO designates a phosphate group; N is any nucleotide, Z is selected from the group consisting of the natural analogues deoxyinosine and deoxyuridine or the synthetic analogues 1-(2'-deoxy-beta-D-ribofuranosyl)-5-nitroindole, 1-(2'-deoxy-beta-D-ribofuranosyl)-3-nitropyrrole or 1-(2'-deoxy-beta-D-ribofuranosyl)-imidazole-4-carboxamide; X is an extension protection group. n2 and m are integers and n2 describes the numbers of N and is larger than or equal to 0 or smaller than or equal to 10 (0≤n2≤10), preferably 0≤n2≤8 and m is larger than or equal to 0 or smaller than or equal to 25 (0≤m≤25) with the proviso that n2 and m together are larger than or equal to 4 or smaller than or equal to 25 (4≤n2+m≤25). A probe or primer can be any stretch of at least 7 or 8, preferably at least 10, more preferably at least 12, 13,14, or 15, such as at least 20, e.g., at least 23 or 25, for instance at least 27 or 30 nucleotides; for instance, between 15 and 25 nucleotides. As to PCR or hybridization primers or probes and optimal lengths therefor, reference is also made to Kajimura et al., GATA 7(4):71–79 (1990).

These unique features of the adaptor ensures that the ligation of the adaptor to a single stranded cDNA will mimic a double stranded ligation reaction. Thus the efficient use of a DNA ligase like T4 DNA ligase can be used in the ligation reaction opposed to the single stranded RNA ligation reaction used in the 'Ligation-anchored PCR' (Troutt et al., 1992). The double stranded overlap will be n2+m bp long and should preferentially be at least 4 bp to mimic a double stranded ligation reaction as also described in a recent paper (Jang & Steffens, 1997).

The adaptors developed by Jang et al. were used only to join small oligo nucleotide sequences and were limited to only six base pairs as they where using degenerated base pairs (N) and not non-selective bases like deoxyinosines. Furthermore, these adaptors were constructed without extension protection groups which probably make them unsuitable for PCR reactions due to unspecific ligation events and the possible elongation of the adaptor sequences during the PCR.

The PCR amplification, which will typically yield at least about 20–40 fold amplification, such as typically about 50 to 100 or 250-fold amplification, but may even be 500 to 1000-fold or higher amplification, can be achieved from as little as some nanograms of cDNA, and is simple to perform under standard molecular biology laboratory conditions Sambrook et al., 1989, Molecular Cloning: A laboratory Manual.

In particular when the cDNA is amplified in the presence of labeled nucleotides, it can be used a sensitive probe in micro array hybridization experiments. The label may be present on any of the primers, the adaptor or the nucleotides used in the amplification process and the label may be selected from the group consisting of fluorophores and radioactive isotopes, such as fluorescein, Cy3, Cy5, rhodamin and Texas Red; or $^{32}$P, $^{33}$P, 35S, $^{3}$H, $^{125}$I and $^{14}$C.

In one general embodiment of the present invention, cDNA strands are synthesized from a collection of mRNAs using a cDNA synthesis primer of the general formula I

   I

Said cDNA synthesis primer is an oligonucleotide primer comprised by a primer region (T$_n$V$_{n1}$) and an anchor region (COM$_1$). If the target mRNA is the entire mRNA population, then the primer region can be a polythymidylate region, e.g., about 7 to 30, preferably about 15 to 20 thymidine (T) residues, i.e. 7≤n≤30 and n1=0 or n1=1. When n1=0 the primer will anneal arbitrarily to the poly-A tail while in the case where n1=1 the primer will preferentially anneal at the junction in the mRNA where the poly-A begins.

The cDNA synthesis primer complex will thus hybridize to the poly(A) tail present on the 3' terminus of each mRNA due to the polythymidylate region. Alternatively, if only a pre-selected mRNA is to be amplified, then the primer or a mixture there off will be designed to be substantially complementary to a section of the chosen mRNA, typically at the 3' terminus upstream of the poly(A) tail, i.e. n=0 and n1=0 and COM$_1$ is designed specifically to anneal to a pre-defined part of the mRNA.

The anchor region (COM$_1$) of the cDNA synthesis primer serves as specific hybridization area for one of the amplification primers (primer #2) in the subsequent amplification reaction of the cDNA.

Once the cDNA synthesis primer hybridizes to the mRNA, a first cDNA strand can be synthesized. This first strand of cDNA is preferably produced through the process of reverse transcription, wherein DNA is made from RNA, utilizing reverse transcriptase following standard techniques. This enzyme, present in all retroviruses (e.g., avian myeloblastoma virus), adds deoxyribonucleotides to the 3' terminus of the primer. These reverse transcriptases might be M-MLV Reverse transcriptase, AMV Reverse Transcriptase or SUPERSCRIPT II Reverse Transcriptase (all available from Life Technologies) or displayTHERMO RT (Display Systems Biotech).

In order to purify the cDNA product of the first strand synthesis for the subsequent ligation step, a spin column is used. This can be any column which allows the separation of small oligonucleotides (less than 100 bp) from larger molecular cDNA species. This step is introduced in order to get rid of excess primers used for the first strand synthesis which would otherwise compete with the single stranded cDNA in the subsequent ligation step.

A specially designed adaptor fragment is ligated to the cDNA product of the first strand synthesis. The adaptor consists of two strands of the general formulas II and III respectively, both strands having complementary overlap regions (COM$_2$ and COM$_4$) of more than 4 residues, such as 5 to 30 residues, preferentially 6 to 25 residues. The first strand (general formula II) is modified with a phosphate group at the 5'-end and a so called extension protection group at the 3'-end. The second strand (general formula II) is modified with an extension protection group at the 3'-end. The specific region (COM$_4$)is followed by 0 to 10 bp, such as 1 to 8 bp, preferably 1 to 4 bp of degenerate residues (N)

and finally 0 to 25 bp, such as 1 to 20, such as 2 to 15, e.g. 3 to 14, e.g. 4 to 13, such as 5 to 12, preferentially 6 to 12 bp of non selective residues (Z). The non-selective residues are preferentially deoxy-inosine or 1-(2'-deoxy-beta-D-ribofuranosyl)-5-nitroindole.

$$5'\text{-PO-COM}_2\text{-COM}_3\text{-X-3'} \quad\quad\quad \text{II}$$

$$5'\text{-COM}_4\text{-(N)}_{n2}\text{-Z}_m\text{-X-3'} \quad\quad\quad \text{III}$$

The phosphate group of strand II of the adaptor fragment serves the purpose of covalently linking this sequence to the 3' end of the cDNA product of the first strand synthesis during the ligation reaction. The extension protection group can be any modification of the 3' end of the two strands in the adaptor fragment which blocks the extension of a nucleic acid sequence by polymerases and avoids the ligation of the 3' end to another nucleic acid sequence. There are two main purposes of the extension protection group. One is to avoid the occurrence of concatamer adaptor sequences during ligation and to limit the ligation events to only one, namely the joining of the 5' end of strand (II) to the 3' of the first strand cDNA synthesis. The other purpose of the extension group is to prevent the two strands (II) and (III) from participating in the downstream PCR reaction where they will still be present. As the two strands are present during the PCR reaction and potentially at high concentration they might also possibly anneal unspecifically to certain cDNA sequences. Thus, if they are devoid of their extension protection group, they might serve as primers and accordingly contribute to unspecific PCR events. Thus, for that reason, the extension protection group is important.

Preferentially the extension protection group is a dideoxynucleotide or a deoxynucleotide that is modified with an amine group at the 3' position, such as aminopropan (3' amine-C3) or aminohexan (3'amine-C6).

The non-selective residues of the adaptor fragment serves the function of providing a sufficient double stranded overlap between the adaptor and the single stranded cDNA to allow the ligation. As the T4 DNA ligase is specific for double stranded DNA this overlap shall be long enough in order for the T4 DNA ligase to work. It should be noted that the annealing temperature of the adaptor should be correlated with the temperature at which the ligation is performed. Thus, when the annealing temperature of the adaptor is between 15° C. and 40° preferentially T4 DNA ligase or *E.coli* DNA ligase should be used. If the adaptor is designed with a high annealing temperature (e.g. above 40°) it can be anticipated that a thermostable ligase like Thermus aquaticus (Taq) DNA ligase with advantage can be used. This ligase is active at elevated-temperatures (45°–65°). This Means that the ligation step of the method can be performed at temperatures from 16° C. to 70° C.

The overlap comprised by the degenerate residues and the non-selective residues should be at least 4 bp. The non-selective residues is preceded by a few (preferably 1–4) selective degenerate residues. These selective degenerate residues are included in order to avoid the adaptor from forming too strong self annealing dimers, inhibiting the ligation reaction.

However, the non-selective residues can not be replaced totally by selective residues, as that would result in a low equilibrium toward the specific single stranded cDNA. For instance a stretch of eight NNNNNNNN would mean that only $1/4^8=1/65536$ part of the adaptor would anneal to a specific sequence. Furthermore a long stretch of N's will result in adaptor mixtures that deviate largely in their annealing temperature. For instance, AAAAAAAA might deviate with up to 16° C. compared to CCCCCCCC in their annealing temperature towards their specific sequence. Thus, a non selective base like deoxyinosine is incorporated into the adaptor in order to keep the annealing temperature of the adaptor constant and also to ensure a high equlibrium toward the specific single cDNA during the ligation.

Essentially any nucleic acid sequence, in purified or non-purified form, can be utilized as the starting nucleic acid(s) for the methods of the present invention, provided it comprises the desired specific nucleic acid sequence (i.e., complementary to the cDNA synthesis primer). It is only generally preferred that a sufficient number of bases at one end of the sequence be known in sufficient detail, so that a primer can be prepared which will hybridize to one of the strands of the desired sequence. A mixture of primers (including specific or degenerated sequences) may also be employed if the more than one nucleic acid sequence is the target.

It is also not necessary that the sequence to be amplified is initially present in a pure form; it may be a minor fraction of a complex mixture, or a portion of a nucleic acid sequence, the existence of which is due to the presence of a particular microorganism. Therefore, the amplification process is useful not only for producing large amounts of one specific nucleic acid sequence, but also for simultaneously amplifying more than one different specific nucleic acid sequence located on the same or different nucleic acid molecule.

The nucleic acid(s) may be obtained from any source, for example, from plasmids such as pBR322, from cloned DNA or RNA, or from natural DNA or RNA from any source, including bacteria, yeast, viruses, organelles, and higher organisms, such as plants or animals. DNA or RNA may be extracted from blood, serum, plasma, cerebrospinal fluid, tissue material/biopsies or cells by a variety of techniques such as those described by Sambrook et al., 1989, Molecular Cloning: A laboratory Manual.

As used herein, the term "cDNA synthesis primer" refers to an oligonucleotide having two components (general formula I): 1) a primer that may be synthetic or purified from a restriction digest of a nucleic acid and 2) an anchor region containing a specific sequence to be used as hybridization target for the amplification primers in the subsequent PCR amplification reaction. The primer component will be capable of acting as a point of initiation of synthesis, typically DNA polymerisation, when placed under conditions in which synthesis of a primer extension product that is complementary to a nucleic acid strand is induced, i.e., in the presence of appropriate nucleotides and a replicating agent (e.g., a DNA polymerase) under suitable conditions, which are described by Maniatis et al.

The primer is preferably a single stranded oligodeoxynucleotide. The primer must be sufficiently long to act as a template for the synthesis of extension products in the presence of the replicating agent. The exact lengths of the primers and the quantities used will depend on many factors, including temperature, degree of homology and other conditions. Preferably, the primer length is between 15 and 25 nucleotides long with an equal distribution of purines and pyrimidines aiming at reaching an annealing temperature between 40–70° C.

For example, when amplifying a specific sequence, the oligonucleotide primer typically contains between about 10 and 50 nucleotides, preferably 15–25 nucleotides. For other applications like differential display (Liang & Pardee, 1992), the oligonucleotide primer is typically, but not necessarily, shorter, e.g., 7–15 nucleotides. Such short primer molecules generally require lower hybridization temperatures to form sufficiently stable hybrid complexes with the template.

The oligonucleotide primers may be prepared using any suitable method, such as, for example, the well known phosphotriester and phosphodiester methods, or automated embodiments thereof. One method for synthesizing oligonucleotides on a modified solid support is described in U.S. Pat. No. 4,458,066. It is also possible to use a primer which has been isolated from a biological source (such as a restriction endonuclease digest).

The primers herein are selected to be "substantially" complementary to the different strands of each specific sequence to be amplified, i.e., the primers should be sufficiently complementary to hybridize with their respective strands at a annealing temperature from 40° to 70° C. Therefore, the primer sequence need not reflect the exact sequence of the template, and can, in fact, be "degenerate." Non-complementary bases or longer sequences can be interspersed into the primer, provided that the primer sequence has sufficient complementarity with the sequence of the strand to be amplified to permit hybridization and extension.

Generally, it is not necessary to know the sequence of a target mRNA, as the primer may be a poly(T) of sufficient length to hybridize with substantially all members of an entire population of mRNAs (i.e., poly(T)$_n$, wherein n is typically from about 5 to 50 or more). Of course, when more sequence knowledge is available for a target RNA, the primer may be designed more specifically, which greatly increases the efficiency of the amplification. If a sequence specific primer is used in the first strand cDNA synthesis, the specific target RNA will preferentially be reverse transcribed. Thus, in the following PCR amplification using the sequence specific primer and a primer specific for the 5'-ligated anchor sequence, this sequence should preferentially be amplified.

Moreover, the primers may actually comprise a collection of primer sequences, such as where more than one target sequence exists. Also, if there is ambiguity in the sequence information, a number of primers should be prepared. In particular, when any of several possible nucleic acid sequences encoding a protein could be correct, based on a polypeptide sequence obtained from a fragment of the protein, a collection of primers containing sequences representing most or all of the possible codon variations (utilizing codon degeneracy) can be prepared.

The techniques of the present invention also provide a number of additional genetic manipulation technologies. The amplified double stranded cDNA represents a useful intermediate for construction of complex cDNA libraries from extremely limited amounts of tissue, such as individual brain nuclei, tissue sections, and even single cells.

Accordingly, the present invention is, in one aspect, directed to the use of the amplification process in a method for detecting expression of a gene in a pre-selected cell population comprising steps of:
(a) synthesizing double-stranded cDNA by treating RNAs from cell populations with a cDNA synthesis primer comprising an oligdnucleotide sequence complementary to one or more of the RNA sequences, followed by reverse transcription of the RNA and ligation of an adaptor to a single stranded cDNA molecule and subsequent PCR amplification as described in detail above,
(b) determining the presence or absence of cDNA complementary to the RNA corresponding to the gene.

The cell population may be, e.g., from a human tissue, such as blood, brain nuclei, liver, prostate, mammary, heart, kidney, lung, testis and pancreas. The tissue may be an embryonic or fetal tissue. The cell population may be single cell, or up to 100 to 1,000,000 cells or more, as desired.

Further, the amplified double stranded cDNA can be used as a source for producing large amounts of single-stranded, anti-sense material for use as driver in subtractive hybridization. For example, two nucleic acid populations, one sense, and one anti-sense, can be allowed to mix together with one population present in molar excess (driver). Sequences present in both populations will form hybrids, whereas sequences present in only one population remain single-stranded (Duguid et al., 1988).

Accordingly, the single stranded cDNA amplification technology can be applied to improve methods of detecting and isolating nucleic acid sequences that vary in abundance among different populations, such as in comparing mRNA expression among different tissues or within the same tissue, according to physiologic state. Methods for examining differential expression typically involve subtractive hybridization, wherein two nucleic acid populations, one sense and one anti-sense, are allowed to mix with one another. One population is present in molar excess ("driver") such that sequences represented in both populations form hybrids, whereas sequences present in only one population remain single-stranded. Thereafter, various well known techniques are used to separate the unhybridized molecules representing differentially expressed sequences.

Most methods of subtractive hybridization require that large amounts (generally between 10–100 micrograms) of nucleic acid are available for use as "driver" in such experiments. This limits usefulness in examining differential expression of mRNAs present in a biological material that is available in small supply. This problem is overcome by cloning the nucleic acid populations of interest prior to subtraction, so that the cloning vector is used to,amplify the amount of nucleic acid available for hybridization. However, because subtraction requires previous cloning, it is complicated, suffers from under- and over- representation of sequences depending on differences in growth rates in the mixed population, and may risk recombination among sequences during propagation of the mixed population. The single stranded cDNA amplification technology of the present invention circumvents these problems by allowing production of large amounts of cDNA from limited amounts of nucleic acid, without the need for previous cloning.

Thus the present invention comprises a method for producing a subtractive hybridization probe comprising:
(a) synthesizing double-stranded cDNA by treating a first mRNA population with a cDNA synthesis primer comprising an oligonucleotide sequence complementary to one or more of the RNA sequences, followed by reverse transcription of the RNA and ligation of an adaptor to the single stranded cDNA molecule and subsequent PCR amplification as described in detail above, wherein primer #1 is modified by biotin in the 5' end,
(b) Isolating the biotin-containing single stranded cDNA (sense) by use of streptavidin coated magnetic beads,
(c) synthesizing double-stranded cDNA by treating a second mRNA population with a cDNA synthesis primer comprising an oligonucleotide sequence complementary to one or more of the RNA sequences, followed by reverse transcription of the RNA and ligation of an adaptor to the single stranded cDNA molecule and subsequent PCR amplification as described in detail above, wherein primer #1 is modified by biotin in the 5' end,
(d) Isolating the non-biotin-containing single stranded cDNA (anti-sense) by use of streptavidin coated magnetic beads, (e) hybridizing the sense to the anti-sense cDNA whereby an unhybridized sub-population of the anti-sense cDNA is found, (f) Isolating the unhybridized sub-population of the anti-sense cDNA by use of streptavidin coated cDNA, (g) generating a second double-stranded cDNA collection from the unhybridized sub-population by PCR using primer #1 and primer #2.

Additionally, the present invention comprises methods for making cDNA libraries from a collection of mRNA molecules which has been reverse transcribed and amplified to double stranded cDNA by primer #1 and primer #2. The double stranded cDNA might be directly ligated into a vector like a TA-cloning vector (Invitrogen) which is transformed into E. coli.

Said method comprising the steps of:

(a) synthesizing double-stranded cDNA by treating a plurality of mRNAs from the cell populations with a cDNA synthesis primer comprising an oligonucleotide sequence complementary to one or more of the RNA sequences, followed by reverse transcription of the RNA and ligation of an adaptor to a single stranded cDNA molecule and subsequent PCR amplification as described in detail above, (b) producing a collection of double-stranded cDNAs by PCR by extending the primers of a plurality of any hybridization duplexes formed between the cDNA (c) preparing a cDNA library from the amplified cDNAs Another application of the technology is the detection of variant regions flanking a common sequence, such as for molecular diagnostics. By designing an amplification primer that recognizes a commonly shared sequence, single stranded cDNA is produced that contains not only the common region recognized by the primer, but also the 5'-anchor sequence which has been ligated to the single stranded cDNA. Thus PCR can be carried out even though only one region of shared sequence is known from the beginning. PCR generally requires that shared sequences to be known both 5'- and 3'- to the region of interest, and that these flanking regions are sufficiently close to allow efficient amplification. Thus, for example, cDNA can be produced from limited amounts of clinical material to allow pathogen-specific sequences (such as those of distinguishing viral types) to be identified, genetic polymorphisms to be detected, or alternate splicing variants to be characterized, all in accordance with standard techniques.

Although the paradigms of the present invention will provide a useful adjunct to PCR in a wide variety of diagnostic or other studies, especially facilitated are studies of gene expression in essentially any mammalian cell or cell population. Although the cell may be from blood (e.g., lymphocytes, such as T or B cells), a typical source of cell or tissue or DNA or nucleotides will be solid organs, such as brain, spleen, bone, heart, vascular, lung, kidney, liver, pituitary, endocrine glands, lymph node, dispersed primary cells, tumor cells, skin, hair, or the like. The cell, tissue etc. may be an embryonic or fetal tissue. Thus, in the neural research area, identification of mRNAs which vary as a function of arousal state, behavior, drug treatment, and development, for example, has been hindered by both the difficulty in construction of cDNA libraries from brain tissue and in the relative spatial insensitivity of subtractive hybridization techniques. Use of the single stranded cDNA amplification method in construction of cDNA libraries from individual brain nuclei will provide for greater representation of low-abundance mRNAs from these tissues compared with their representation in whole brain cDNA libraries, and facilitate cloning of important low-abundance messages.

The materials for use in the methods of the present invention are ideally suited for preparing of kits, produced in accordance with well known procedures, and are therefore readily provided in kit form for a variety of uses. Such a kit may comprise containers, each with one or more of the various reagents (typically in concentrated form) utilized in the methods, including, for example, buffers, the appropriate nucleotide triphosphates (e.g., dATP, dCTP, dGTP and dTTP; or rATP, rCTP, rGTP and UTP) which may be labeled, such as with fluorophores or radioactive labels (e.g. fluorescein, Cy3, Cy5, rhodamin and Texas Red; or $^{32}P$, $^{33}P$, $^{35}S$, $^{3}H$, $_{125}I$ and $^{14}C$ and the like), reverse transcriptase, DNA polymerase, T4 DNA ligase, the adaptor and one or more primer complexes of the present invention (e.g., appropriate length poly(T) or random primers linked to a promoter reactive with the RNA polymerase). A set of instructions will also typically be included.

EXAMPLES

Example 1

Preferred method for constructing a probe for micro-array hybridization

Materials

Reverse transcriptase (displayTHERMO), T4 DNA ligase, TAQ DNA polymerase (displayTAQ FL) were obtained from Display Systems Biotech. Fluorescent dideoxy-nucleotides (Cy3 - and Cy5-dNTP) were purchased from Amersham-Pharmacia. PCR purification columns from Qiagen (QIAquick PCR Purification kit—Cat. no.28104). Rat heart and lung RNA from Clontech laboratories.

cDNA Synthesis

In 25 $\mu$l volume of cDNA synthesis buffer (50 mM Tris-HCL, pH 8.3; 80 mM KCl; 10 mM $Cl_2$; 4 mM DTT), 500 ng total RNA was reverse transcribed with 0.75 mM of the cDNA synthesis primer as seen in FIG. 2, step 1:

5' GCA CTG GTA ACA ACG CAG GA TTT TTT TTT TTT TTT TTT V (SEQ ID NO: 1)

including 1 mM dNTP and 1 Unit Reverse transcriptase. The reaction was incubated for 1 hour and 30 min at 42° C. followed by 15 min incubation at 65C.

Spin Column Purification

The 25 $\mu$l first strand cDNA synthesis was purified by use of a spin column from Qiagen (QIAquick PCR Purification kit—Cat. no. 28104) following the protocol as described and eluted using 30 $\mu$l $H_2O$). The synthesized cDNA strand is shown in FIG. 2, step 2).

Adaptor Ligation

To 11.7 $\mu$l purified first strand synthesis reaction 1.5 $\mu$l 10× Ligation buffer was added (100 mM Tris-acetate; 100 mM Magnesium-acetate; 500 mM Potassium-acetate; 3 mM ATP), 0.3 $\mu$l T4 DNA ligase. Finally 1.5 $\mu$l of an adaptor (10 $\mu$M) was added as shown in FIG. 2, step 3) and the reaction was incubated at 37° C. for 3 hours. The resulting single stranded DNA is pictured in FIG. 2, step 4) and 5). This concentration of the adaptor will ensure that it is present in at least 10 fold molar excess, assuming that all 500 ng RNA is reverse transcribed to single stranded cDNA. When total RNA is used (as in this example) the molar excess will be even larger as preferentially the mRNA will be reverse transcribed.

The adaptor was prepared by mixing

5' GCA TCT GAC GCA TGC NNN NII III III I-amine C3 (SEQ ID NO: 2)

5' $PO_4$-GCA TGC GTC AGA TGC TCT CGG CAG TCC TGA GTA GCG A-amine C3 (SEQ ID NO: 3)

This reaction was then ready to be used directly in a PCR reaction for amplification, with primers #1 and primer #2, as shown in FIG. 2, step 6–9).

Checkpoint to Confirm Adaptor Ligation

This step verifies the ligation reaction. A 'cold' PCR reaction is performed in the following way. 2 μl 10× Taq polymerase buffer (100 mM Tris-HCl pH 8.3, 500 mM KCl, 15 mM MgCl$_2$) is mixed with 2 μl 2 μm primer #1: 5' TCGCTACYCAGGACTGCC (SEQ ID NO: 4) and 2 μl 12 μM primer #2: 5' GCA CTG GTA ACA ACG CAG G (SEQ ID NO: 5), 0.8 μl dNTP mix (5 mM), 2 μl of the template from the adaptor ligation, 10.95 μl H2O and 0.25 μl display TAQ FL. The following PCR profile is performed:

| Denature: at | 94° C., 30 sec |
| --- | --- |
| | 55° C., 30 sec, |
| | 72° C., 1 min. |

Continue another 20 cycles with the following sequence:

| 94° C., 30 sec |
| --- |
| 60° C., 30 sec |
| 72° C., 1 min |

This result is shown in FIG. 3.

PCR Amplification With Fluorescent Labels

The following PCR reaction is performed in duplicate: 5.0 μl 10× Taq polymerase buffer (100 mM Tris CHl pH 8.3, 500 mM KCl, 15 mM MgCl2) was mixed with 5 μl 2 μm primer #1: 5' TCGCTACTCAGGACTGCC (SEQ ID NO: 4), 5 μl 12 μM primer #2: 5' GCA CTG GTA ACA ACG CAG G (SEQ ID NO: 5), 2.0 μl labeling mix (5 mM dATP; 5 mM dCTP; 5 mM dGTP; 3.5 mM Dttp), 5 μl of the template from the adaptor ligation, 24.5 μl H2O and 0.5 μl display TAQ FL. Primer #2 is present in 6 fold molar excess compared to primer #1 with the purpose of performing the PCR with a skewed ratio of amplification primers is to end up with an excess of one of the labeled single stranded strand. In this case the single strand complementary to the original RNA population will be in excess. The use of a single stranded probe in micro-array hybridization is much more efficient compared to a double strand probe where a much larger fraction will re-anneal during the hybridization.

The following PCR profile is performed:

| Denature: at | 94° C., 30 sec |
| --- | --- |
| | 55° C., 30 sec, |
| | 72° C., 1 min. |

Continue another 20 cycles with the following sequence:

| 94° C., 30 sec |
| --- |
| 60° C., 30 sec |
| 72° C. 1 min |

5 μl of each reaction is checked on an agarose gel

Precipitation of the Probe for Hybridization

The 2×45 μl PCR reaction was pooled, 10 μl 3 M NaOAc is added together with 200 μl absolute ethanol. After centrifugation at 14000×g at room temperature for 20 min, the pellet is washed with 400 μl 80% ethanol. The pellet was dried and was then ready for hybridization.

Hybridization

The probe is analyzed using slides manufactured by Display Systems Biotech (cat. no. 410-101) which contain about 2800 mouse genes. The pellet is resuspended in 30 μl hybridization buffer, denatured at 95° C. for 3 min and gently placed on the gene slide and hybridized with under a cover glass for 20 hours at 65° C. The slide cover glass was gently removed using 2×SSC. The slide was washed for 2×10 min at 65° C. using 2×SSC, followed by a wash for 3 min at room temperature in 0.2×SSC, 3 min in 0.1×SSC and finally by 4×1 min. at room temperature. The slide was finally dried by spinning down at 3 min at 800 rpm.

Array Data Analysis

Using a confocal scanning microscope (Affymetrix), the hybridized array slide was scanned in two steps, first using a red laser for the Cy5 dye and secondly using a green laser for the Cy3 dye. The resulting two image files were subsequently used for further data analysis. The resulting image file can be seen in FIG. 4.

Example2

Use of the Method for Cluster Analysis

Materials

Reverse transcriptase (Cat #570-100), T4 DNA ligase, TAQ DNA polymerase (Cat #550-100) were obtained from Display Systems Biotech. Fluorescent dideoxy-nucleotides (Cy3- and Cy5-dNTP) were purchased from Amersham-Pharmacia. PCR purification colums from Qiagen (QlAquick PCR purification kit—Cat. No. 28194).

Treatment of Mice and RNA Isolation

Male mice (NMRI, 13–14 weeks of age) were treated with the compounds Fluoxetin (15 mg/kg), Clomipramine (20 mg/kg), Desipramine (20 mg/kg) and Fluvoxamine (10 mg/kg). Following treatment, the brain and the pituitary were collected and rapidly frozen on dry ice. Total RNA was extracted using the phenol-chloroform extraction method (Chomczynski and Sacchi, 1987). The RNA was evaluated on a gel, and only RNA showing distinct ribosomal bands on this gel was used for further analysis.

Labeling of RNA

60 μg of pituitary RNA were used in the labeling of the four RNA samples using a standard reverse transcription method as described in the displayTRACKER manual (Display Systems Biotech, cat #490-100)—denoted as samples 1a–4a. One microgram of the whole brain RNA samples were labeled using the method as described in detail in Example 1 (sample 1b–4b). The labeled samples are described in Table I.

TABLE I

Labeling of RNA

| Identity | Drug used in treatment | Cy3 | Cy5 | Method used | Amount of total RNA used/μg |
| --- | --- | --- | --- | --- | --- |
| 1a | Desipramine | Control | Treated | 'Standard' | 60 |
| 2a | Clomipramine | Control | Treated | 'Standard' | 60 |
| 3a | Fluoxetine | Control | Treated | 'Standard' | 60 |
| 4a | Fluvoxamine | Control | Treated | 'Standard' | 60 |
| 1b | Desipramine | Control | Treated | New method | 1 |
| 2b | Clomipramine | Control | Treated | New method | 1 |
| 3b | Fluoxetine | Control | Treated | New method | 1 |
| 4b | Fluvoxamine | Control | Treated | New method | 1 |

The probes were analyzed using slides manufactured by Display Systems Biotech containing spots corresponding to about 6000 gene fragments. The microarrays were constructed by combining the approximately 5400 gene fragments from the mouse I discovery (Display Systems Biotech, cat #410-101) and mouse II discovery array (Display Systems Biotech, cat #410-102) together with 960 clones from Research Genetics (plate 1-10; cat #97001.MmV). In total, a microarray consisting of approximately 6500 spots were obtained. The preparation of the microarray was carried out using the same conditions as for the Mouse I and II discovery arrays.

Array Data Analysis

The arrays were scanned and using a so-called cluster analysis program, (GeneSight 2.0, Biodiscovery) the array data were analyzed. The result of the cluster analysis is shown in FIG. 5a, and FIG. 5b. The cluster analysis program was used to group gene expression data based on their similarity (Young, 2000). Thus, the effect on gene expression of different drugs can be clustered in this way. If two drugs shares the same mechanism it can be expected that they will cluster together as they will regulate the same genes. This is seen in FIG. 5a and FIG. 5b where the effect of drug 2 and drug 4 cluster together as they regulate similar genes. It can be seen that the clustering of the drugs gives the same results independent of the method used. The clustering of the genes (listed vertically) is however not exactly identical which is expectable since the two methods do not reflect identical degrees of regulations. However, the overall general picture is that the same regulated genes are detected using the two independent methods. Thus, two figures shows that the new method can be used on 1.0 μg RNA with similar results when compared with the 'standard' method which uses 60 pg RNA.

FURTHER DESCRIPTION OF THE INVENTION

The invention shall now be further described in the following numbered paragraphs:

1. A method for synthesizing a single stranded cDNA by a 5'-ligated adaptor-mediated process, said method comprising a) annealing a cDNA synthesis primer of the general formula I $$5'\text{-COM}_1 T_n V_{n1}\text{-}3'\qquad\qquad \text{I}$$

to an RNA molecule and synthesizing a first cDNA strand to form an RNA-cDNA intermediate, wherein $COM_1$ is a pre-selected nucleotide sequence larger than or equal to 0 nucleotides long, n and n1 are integers, $0 \leq n$ and $0 \leq n1 \leq 1$, T is thymidine, and V is a nucleotide selected from the group consisting of A, G, and C, b) separating the cDNA strand from the RNA, c) purifying the cDNA by removing the excessive cDNA synthesis primer, d) contacting said cDNA with an adaptor, said adaptor consisting of two oligonucleotides hybridized to each other having the general formula II and III respectively $$5'\text{-PO-COM}_2\text{-COM}_3\text{-X-}3'\qquad\qquad \text{II}$$

$$5'\text{-COM}_4\text{-(N)}_{n2}\text{-Z}_m\text{-X-}3'\qquad\qquad \text{III}$$

said oligonucleotides forming the complex

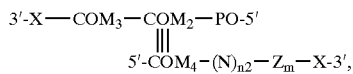

wherein $COM_2$, $COM_3$ and $COM_4$ are pre-selected nucleotides sequences, $COM_2$ and $COM_4$ are complementary to each other, PO is a phosphate group, N is any nucleotide, Z is selected from the group consisting of the natural analogues deoxyinosine and deoxyuridine or the synthetic analogues 1-(2'-deoxy-beta-D-ribofuranosyl)-5-nitroindole, 1-(2'-deoxy-beta-D-ribofuranosyl)-3-nitropyrrole or 1-(2'-deoxy-beta-D-ribofuranosyl)-imidazole-4-carboxamide, X is an extension protection group, $0 \leq n2 \leq 10$, $0 \leq m \leq 25$ with the proviso that $4 \leq n2+m \leq 25$, $COM_3$ is larger than or equal to 0 nucleotides and both $COM_2$ and $COM_4$ are of equal length and larger than or equal to 4 nucleotides, e) ligating the adaptor via the 5'-phosphate group on strand II of the adaptor to the single stranded cDNA using a DNA ligase, f) amplifying said ligated single stranded cDNA fragment obtained in step e) in a molecular amplification procedure so as to obtain amplified cDNA fragments, wherein is used at least one set of amplification primers (primer #1 and primer #2) being partly or fully complementary to the general formula II and the pre-selected nucleotide sequence ($COM_1$) of the anchor region of the cDNA synthesis primer respectively.

2. A method according to paragraph 1, wherein the $COM_1$ sequence and the $COM_3$ sequence are identical.

3. A method according to any one of paragraphs 1 or 2, wherein $0 \leq n \leq 50$, $10 \leq COM_1 \leq 40$, $10 \leq COM_3 \leq 40$, $4 \leq COM_2 \leq 50$, $4 \leq COM_4 \leq 50$, $0 \leq n2 \leq 8$ and $0 \leq m \leq 15$.

4. A method according to any one of the preceding paragraphs, wherein $7 \leq n \leq 30$, $15 \leq COM_1 \leq 30$, $15 \leq COM_3 \leq 30$, $10 \leq COM_2 \leq 30$, $10 \leq COM_4 \leq 30$, $0 \leq n2 \leq 6$ and $0 \leq m \leq 10$.

5. A method according to any one of the preceding paragraphs, wherein n=18, n1=1, $COM_1$=20, $COM_3$=22, $COM_2$=15, $COM_4$=15, n2=4 and m=9.

6. A method according to any one of paragraphs 1–3, wherein n=0.

7. A method according to any one of paragraphs 1–3, wherein n1=0.

8. A method according to any one of the preceding paragraphs, wherein the temperature in the ligation reaction step e) is between 16° C.–70° C.

9. A method according to paragraph 8, wherein the ligation temperature is 37° C.

10. A method according to any one of paragraphs 1–9, wherein the cDNA synthesis primer of the general formula I is labeled.

11. A method according to any one of paragraphs 1–9, wherein the oligonucleotide of the adaptor having the general formula II is labeled.

12. A method according to any one of paragraphs 10 or 11, wherein the label is selected from the group consisting of fluorophores and radioactive isotopes 13. A method according to paragraph 12, wherein the fluorophore is selected from the group consisting of fluorescein, Cy3, Cy5, rhodamin and Texas Red.

14. A method according to paragraph 12, wherein the radioactive isotope is selected from the groupconsisting of $^{32}P$, $^{33}P$, $^{35}S$, $^{3}H$ $^{125}I$ and $^{14}C$.

15. A method according to any of the preceding paragraphs, wherein the DNA ligase is T7 DNA ligase.

16. A method according to any one of the preceding paragraphs, wherein the RNA is a mRNA.

17. A method for making a cDNA library from a collection of mRNA molecules in a sample, wherein a method according to any one of the preceding paragraphs is applied to amplify the cDNAs corresponding to the mRNAs by annealing one or more cDNA synthesis primers to the plurality of mRNAs in the sample.

18. A method for detecting expression of a gene in a pre-selected cell population comprising steps of:
   a) synthesizing single-stranded cDNA according to any one of paragraphs 1 to 16,
   b) determining the presence or absence of cDNA complementary to the RNA corresponding to the gene of interest.

19. A method according to paragraph 18, wherein the presence or absence of cDNA complementary to the RNA corresponding to the gene of interest is determined by electrophoresis.

20. A method according to paragraph 19, wherein the electrophoresis is selected from the group consisting of polyacrylamid gel electrophoresis (PAGE), agarose gel electrophoresis and capillary electrophoresis system.

21. A method according to paragraph 18, wherein the presence or absence of cDNA complementary to the RNA corresponding to the gene of interest is determined by real time fluorescence detection in a PCR light cycler.

22. A method for producing a subtractive hybridization probe comprising:
   a) synthesizing a double-stranded cDNA collection from a first mRNA population according to any one of paragraphs 1 to 16, wherein primer #1 is modified by biotin in the 5' end,
   b) Isolating the biotin-containing single stranded cDNA (sense) by use of streptavidin coated magnetic beads,
   c) synthesizing a double-stranded cDNA collection from a second mRNA population according to paragraph 1 to 16, where primer #1 is modified by biotin in the 5' end,
   d) Isolating the non-biotin-containing single stranded cDNA (anti-sense) by use of streptavidin coated magnetic beads,
   e) hybridizing the sense to the anti-sense cDNA whereby an unhybridized sub-population of the anti-sense cDNA is found,
   f) Isolating the unhybridized sub-population of the anti-sense cDNA by use of streptavidin coated cDNA,
   g) generating a second double-stranded cDNA collection from the unhybridized sub-population by PCR using primer #1 and primer #2.

23. A method for detecting variant regions flanking a common sequence, such as for molecular diagnostics by designing an amplification primer recognizing a commonly shared sequence, single stranded cDNA is produced that contains not only the common region recognized by the primer, but also a 5'-flanking sequence useful in detecting sequence variants by PCR amplification with the region specific primer and primer #1.

24. A method for cloning 5'-ends of genes, wherein the amplified cDNA corresponding to the 5'-ends of the gene of interest is synthesized by a method according to any one of paragraphs 1–16.

25. A method according to any of the preceding paragraphs, wherein the source of nucleic acid is selected from the group consisting of blood, serum, plasma, cerebrospinal fluid, urine, tissue samples, biopsies and saliva.

26. A method according to paragraph 25, wherein the tissue sample is selected from the group consisting of brain, spleen, bone, heart, vascular, lung, kidney, liver, pituitary, endocrine glands, lymph node and dispersed primary cells.

27. A method according to paragraphs 25 or 26, wherein the tissue sample is comprised by a cell population said cell population being characterized may be single cell, or up to 100 to 1,000,000 cells or more as desired.

28. A kit comprising the materials for use in the method according to any one of paragraphs 1–27.

29. A kit according to paragraph 28 comprising containers, each with one or more of the various reagents (typically in concentrated form) utilized in the method, including buffers, the appropriate nucleotide triphosphates selected from the group consisting of dATP, dCTP, dGTP and dTTP; or rATP, rCTP, rGTP and UTP, said nucleotide triphosphates may be labeled with fluorophores or radioactive labels selected from the group consisting of fluorescein, Cy3, Cy5, rhodamin, Texas Red, $^{32}P$, $^{33}P$, $^{35}S$, $^{3}H$, $^{125}I$ and $^{14}C$, reverse transcriptase, DNA polymerase, T4 DNA ligase, the adaptor and one or more primer complexes and a set of instructions.

BRIEF DESCRIPTION OF THE FIGURES

FIG. 2. Schematic representation of the method for amplification of cDNA described in example 1.

Figure 1:
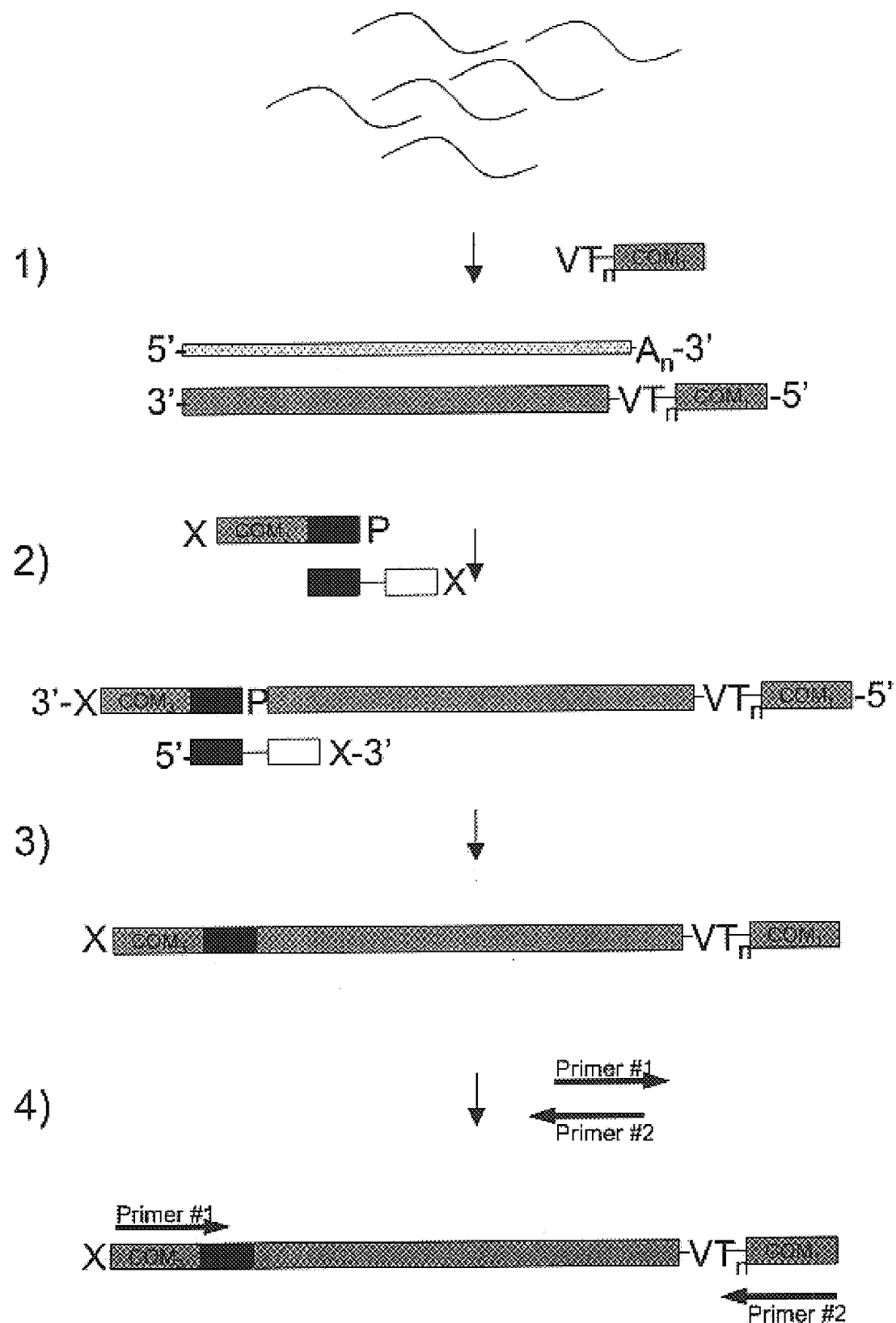
FIG. 1. Schematic representation of the method for amplification of cDNA. 1.) Whole RNA is reverse transcribed using an anchored synthetic primer $T_n V\text{-}COM_1$ primer, 2) followed by hybridizing an adaptor to the single stranded first strand cDNA, 3) ligating the adaptor to the single stranded cDNA, and 4) amplifying the ligated single stranded cDNA with primers #1 and #2.
Figure 3:
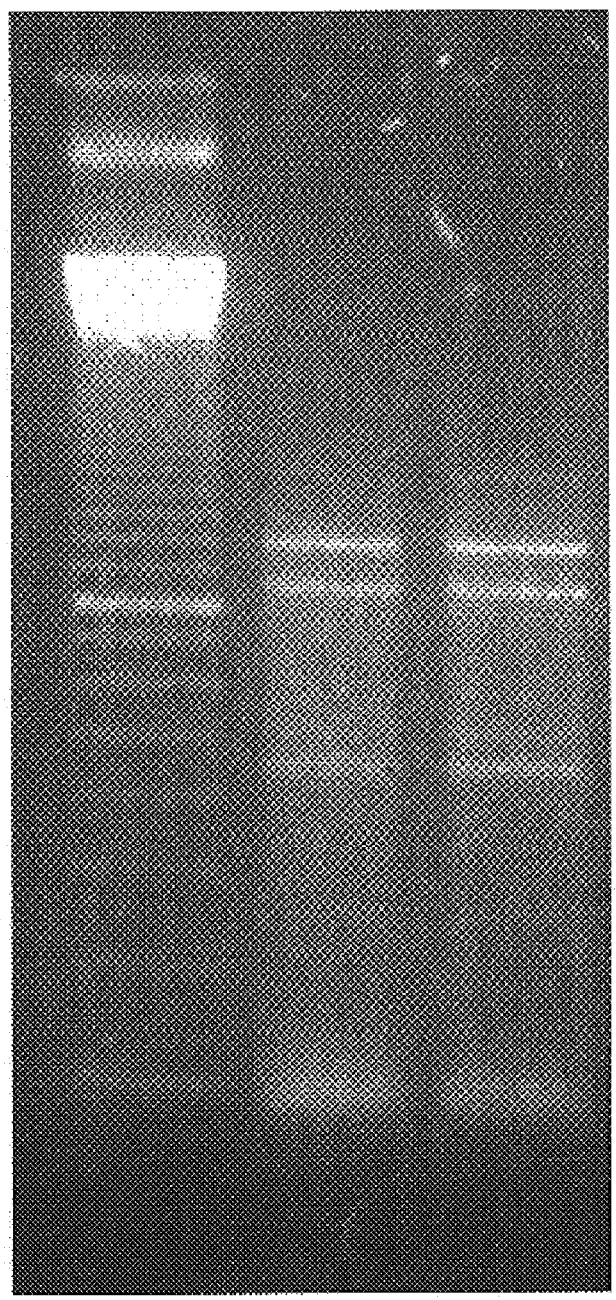
FIG. 3. PCR amplification of single stranded cDNA. After first strand synthesis and adaptor ligation, the single stranded cDNA is PCR amplified by two specific primers.
Figure 4:
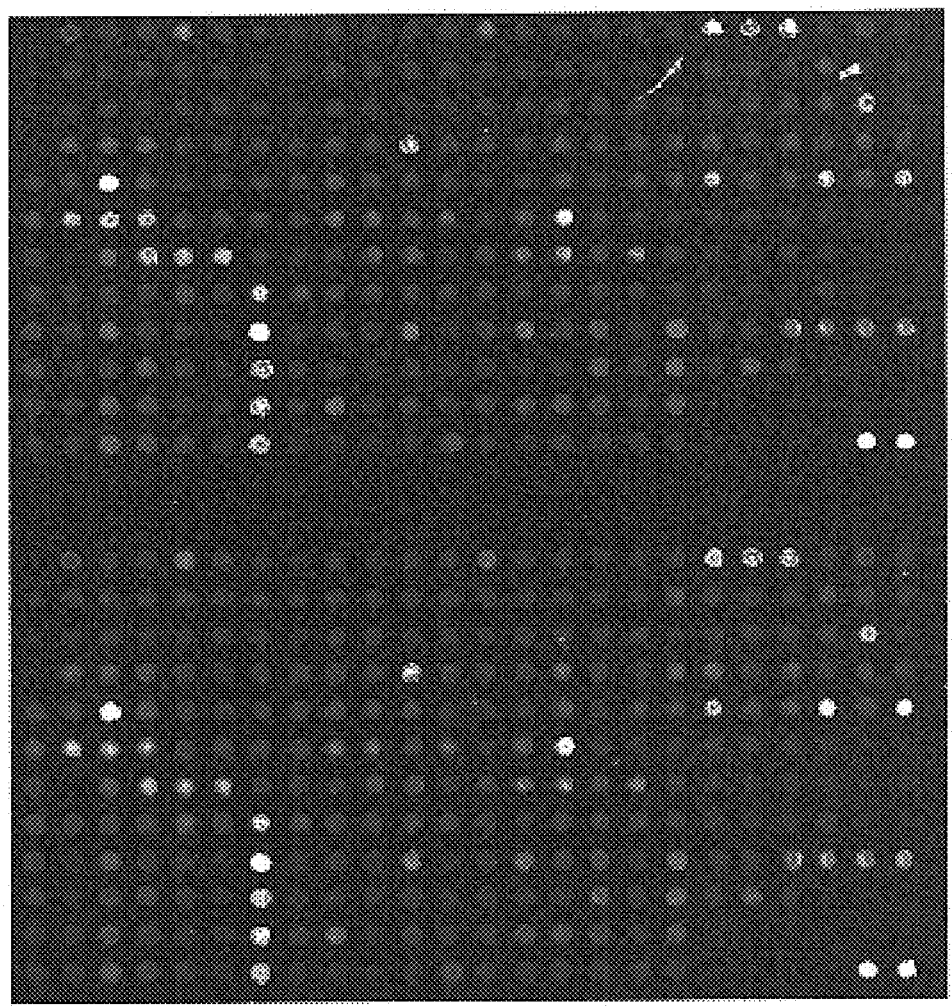
FIG. 4. Hybridization of an amplified probe toward a cDNA array.
Figure 5A:
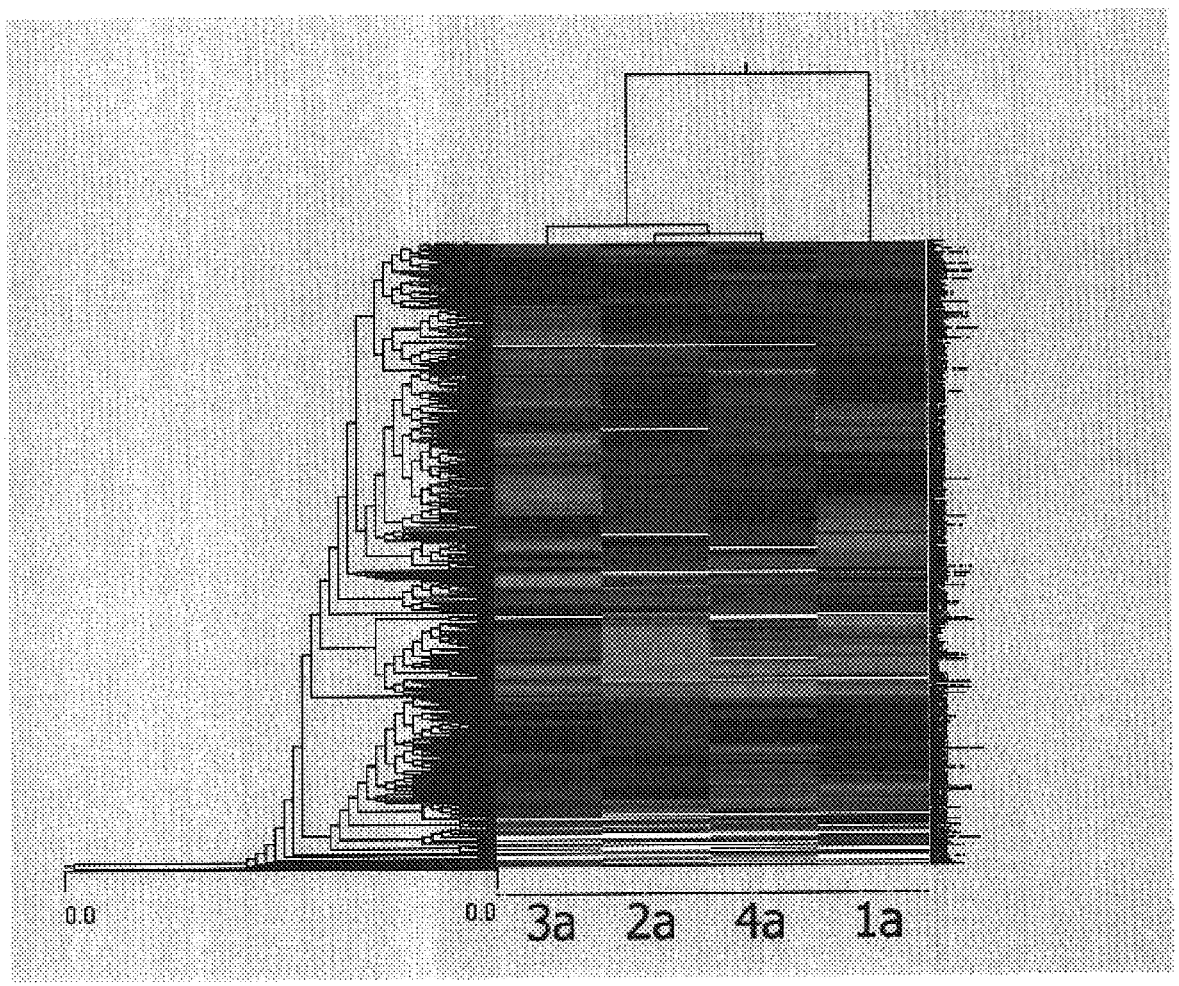
FIG. 5a and 5b. Cluster analyses of arrays using a cluster analysis program (GeneSight 2.0, Biodiscovery), showing that the inventive method can be used on 1.0 μg RNA to obtain similar results similar to those of a 'standard' method which uses 60 μg RNA, demonstrating the surprising superiority of the present invention.
Figure 5B:
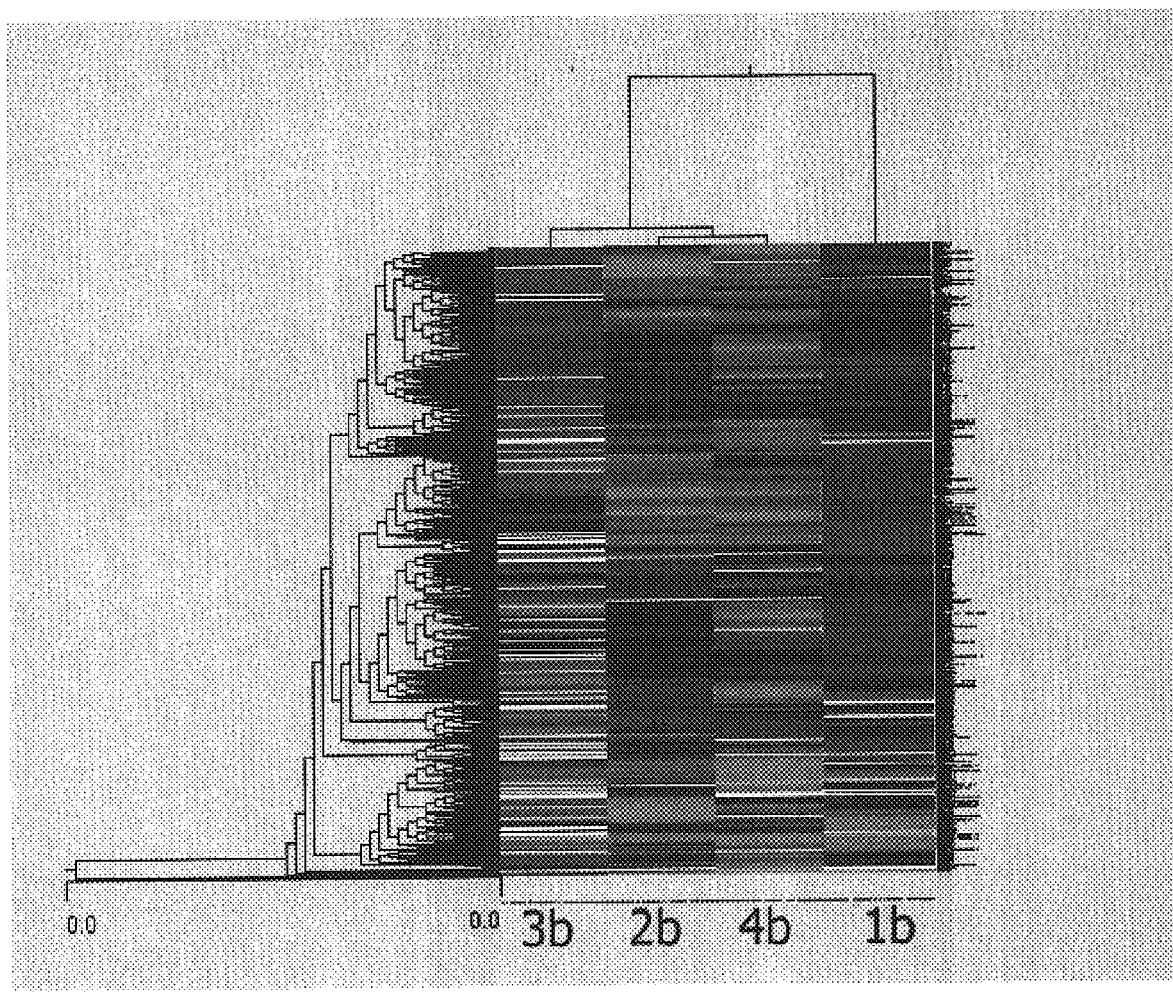

The file of this patent contains at least one drawing executed in color. Copies of this patent with color drawing(s) will be provided by the Patent and Trademark Office upon request and payment of the necessary fee.

REFERENCE LIST

Duguid, J. R., Rohwer, R. G., & Seed, B. (1988). Isolation of cDNAs of scrapie-modulated RNAs by subtractive hybridization of a cDNA library. *Proc. Natl. Acad. Sci. U. S. A* 85, 5738–42.

Frohman, M. A., Dush, M. K., & Martin, G. R. (1988). Rapid production of full-length cDNAs from rare transcripts: amplification using a single gene-specific oligonucleotide primer. *Proc. Natl. Acad. Sci. U. S. A* 85, 8998–9002.

Gould, S. J., Subramani, S., & Scheffler, 1. E. (1989). Use of the DNA polymerase chain reaction for homology probing: isolation of partial cDNA or genomic clones encoding the iron-sulfur protein of succinate dehydrogenase from several species [published erratum appears in Proc Natl Acad Sci U S A 1993 Mar 15;90(6):2556]. *Proc. Natl. Acad. Sci. U. S. A* 86, 1934–8.

Jang, G. Y. & Steffens, D. L. (1997). Ligation mediated fluorescent labeling of DNA sequencing primers. *Nucleic Acids Res.* 25, 922–3.

Liang, P. & Pardee, A. B. (1992). Differential display of eukaryotic messenger RNA by means of the polymerase chain reaction [see comments]. *Science* 257, 967–71.

Trenkle, T., Welsh, J., & McClelland, M. (1999). Differential display probes for cDNA arrays. *Biotechniques* 27, 554–60, 562, 564.

Troutt, A. B., McHeyzer-Williams, M. G., Pulendran, B., & Nossal, G. J. (1992). Ligation-anchored PCR: a simple amplification technique with single-sided specificity [published erratum appears in Proc Natl Acad Sci U S A 1993 Apr, 15;90(8):3775]. *Proc. Natl. Acad. Sci. U. S. A* 89, 9823–5.

Richard A. Young (2000). Biomedical Discovery with DNA arrays. Cell, 102, 9–15

What is claimed is:

1. A method for synthesizing a single stranded cDNA by a 5'-ligated adaptor-mediated process, said method comprising a) annealing a cDNA synthesis printer of the general formula I $$5'\text{-}COM_1T_nV_{n1}\text{-}3' \qquad \text{I}$$

to an RNA molecule and synthesizing a first cDNA strand to form an RNA-cDNA intermediate, wherein $COM_1$ is a known nucleotide sequence from 1 to 40 nucleotides, n and n1 are integers, $0 \leq n$ and $0 \leq n1 \leq 1$, T is thymidine, and V is a nucleotide selected from the group consisting of A, G, and C, b) separating the cDNA strand from the RNA, c) purifying the cDNA by removing the excessive cDNA synthesis primer, d) contacting said cDNA with an adaptor, said adaptor consisting of two oligonucleotides hybridized to each other having the general formula II and III respectively $$5'\text{-}PO\text{-}COM_2\text{-}COM_3\text{-}X\text{-}3' \qquad \text{II}$$

$$5'\text{-}COM_4\text{-}(N)_{n2}\text{-}Z_m\text{-}X\text{-}3' \qquad \text{III}$$

said oligonucleotides forming the complex $$\begin{array}{c}3'\text{-}X\text{---}COM_3\text{---}COM_2\text{---}PO\text{-}5'\\|||\\5'\text{-}COM_4\text{-}(N)_{n2}\text{---}Z_m\text{---}X\text{-}3',\end{array}$$

wherein $COM_2$, $COM_3$ and $COM_4$ are known nucleotides sequences, $COM_2$ and $COM_4$ are complementary to each other, PO is a phosphate group, N is any nucleotide, Z is selected from the group consisting of the natural analogues deoxyinosine and deoxyuridine or the synthetic analogues 1-(2'-deoxy-beta-D-ribofuranosyl)-5-nitroindole, 1-(2'-deoxy-beta-D-ribofuranosyl)-3-nitropyrrole or 1-(2'-deoxy-beta-D-ribofuranosyl)-imidazole-4-carboxamide, X is an extension protection group, $0 \leq n2 \leq 10$, $0 \leq m \leq 25$ with the proviso that $4 \leq n2+m \leq 25$, $COM_3$ is at least 10 up to 40 nucleotides and both $COM_2$ and $COM^4$ are of equal length and larger than or equal to 4 up to 50 nucleotides, e) ligating the adaptor solely via the 5'-phosphate group on strand II of the adaptor to the single stranded cDNA using a DNA ligase, and f) amplifying said ligated single stranded cDNA fragment obtained in step e) in a molecular amplification procedure so as to obtain amplified cDNA fragments, with at least one set of amplification primers (primer #1 and primer #2) being partly or fully complementary to the general formula II and the known nucleotide sequence ($COM_1$) of the anchor region of the cDNA synthesis primer respectively.

2. The method according to claim 1, wherein the $COM_1$ sequence and the $COM_3$ sequence are identical.

3. The method according to claim 1, wherein the number of nucleotides of $COM_1$, the number of nucleotides of $COM_2$, the number of nucleotides of $COM_4$ and the values for n, n2 and m are: $0 \leq n50$, $10 \leq COM_1 \leq 40$, $4 \leq COM_2 \leq 25$, $4 \leq COM_4 \leq 25$, $0 \leq n2 \leq 8$ and $0 \leq m \leq 15$.

4. The method according to claim 1, wherein the number of nucleotides of $COM_1$, the number of nucleotides of $COM_2$, the number of nucleotides of $COM_3$, the number of nucleotides of $COM_4$ and the values for n, n2 and m are: $7 \leq n \leq 30$, $15 \leq COM_1 \leq 30$, $15 \leq COM_3 \leq 30$, $10 \leq COM_2 \leq 30$, $10 \leq COM_4 \leq 30$, $0 \leq n2 \leq 6$ and $0 \leq m \leq 10$.

5. The method according to claim 1, wherein n=18, n1=1, $COM_1$=20, $COM_3$=22, $COM_2$=15, $COM_4$=15, n2=4 and m=9.

6. The method according to claim 1, wherein n=0.

7. The method according to claim 1, wherein n1=0.

8. The method according to claim 1, wherein the temperature in the ligation reaction step c) is between 16° C.–70° C.

9. The method according to claim 8, wherein the ligation temperature is 37° C.

10. The method according to claim 1, wherein the cDNA synthesis primer of the general formula I is labeled.

11. The method according to claim 1, wherein the oligonucleotide of the adaptor having the general formula II is labeled.

12. The method according to claim 10, wherein the label is selected from the group consisting of fluorophores and radioactive isotopes.

13. The method according to claim 11, wherein the label is selected from the group consisting of fluorophores and radioactive isotopes.

14. The method according to claim 12, wherein the fluorophore is selected from the group consisting of fluorescein, Cy3, Cy5, rhodamin and Texas Red.

15. The method according to claim 13, wherein the fluorophore is selected from the group consisting of fluorescein, Cy3, Cy5, rhodamin and Texas Red.

16. The method according to claim 14, wherein the radioactive isotope is selected from the group consisting of $^{32}P$, $^{33}P$, $^{35}S$, $^{3}H$, $^{125}I$ and $^{14}C$.

17. The method according to claim 15, wherein the radioactive isotope is selected from the group consisting of $^{32}P$, $^{33}P$, $^{35}S$, $^{3}H$, $^{125}I$ and $^{14}C$.

18. The method according to claim 1, wherein the DNA ligase is T7 DNA ligase.

19. The method according claim 1, wherein the RNA is a mRNA.

20. A method for making a cDNA library from a collection of mRNA molecules in a sample, wherein the method according to claim 1 is applied to amplify the cDNAs corresponding to the mRNAs by annealing one or more cDNA synthesis primers to the plurality of mRNAs in the sample.

21. A method for producing a subtractive hybridization probe comprising:

a) synthesizing a double-stranded cDNA collection from a first mRNA population according claim 1, wherein primer #1 is modified by biotin in the 5' end, b) isolating the biotin-containing single stranded cDNA (sense) by use of streptavidin coated magnetic beads, c) synthesizing a double-stranded cDNA collection from a second mRNA population according to claim 1 to 16, wherein primer #1 is modified by biotin in the 5' end, d) isolating the non-biotin-containing single stranded cDNA (anti-sense) by use of streptavidin coated magnetic beads, e) hybridizing the sense to the anti-sense cDNA whereby an unhybridized sub-population of the anti-sense cDNA is found, f) isolating the unhybridized sub-population of the antisense cDNA by use of streptavidin coated cDNA, and g) generating a second double-stranded cDNA collection from the unhybridized sub-population by PCR using primer #1 and primer #2.

22. A method according to claim 1, wherein the source of nucleic acid is selected from the group consisting of blood, serum, plasma, cerebrospinal fluid, urine, tissue samples, biopsies and saliva.

23. The method according to claim 22, wherein the tissue sample is selected from the group consisting, of brain, spleen, bone, heart, vascular, lung, kidney, liver, pituitary, endocrine glands, lymph node and dispersed primary cells.

24. The method according to claim 23, wherein the tissue sample is comprised by a, cell population said cell population being characterized may be single cell, or up to 100 to 1,000,000 cells or more as desired.

* * * * *

SEQUENCE LISTING

```
<160> NUMBER OF SEQ ID NOS: 19

<210> SEQ ID NO 1
<211> LENGTH: 39
<212> TYPE: DNA
<213> ORGANISM: Artificial Sequence
<220> FEATURE:
<223> OTHER INFORMATION: cDNA from reverse transciption of RNA
<221> NAME/KEY: misc_feature
<222> LOCATION: (39)..(39)
<223> OTHER INFORMATION: V is a nucleotide selected from the group of A,
      G, and C

<400> SEQUENCE: 1
gcactggtaa caacgcagga tttttttttt tttttttv                              39

<210> SEQ ID NO 2
<211> LENGTH: 28
<212> TYPE: DNA
<213> ORGANISM: Artificial Sequence
<220> FEATURE:
<223> OTHER INFORMATION: First component of adaptor for creating single
      strand DNA
<221> NAME/KEY: misc_feature
<222> LOCATION: (16)..(19)
<223> OTHER INFORMATION: N is any nucleotide
<221> NAME/KEY: misc_feature
<222> LOCATION: (20)..(28)
<223> OTHER INFORMATION: W is deoxyinosine

<400> SEQUENCE: 2
gcatctgacg catgcnnnnw wwwwwwww                                         28

<210> SEQ ID NO 3
<211> LENGTH: 37
<212> TYPE: DNA
<213> ORGANISM: Artificial Sequence
<220> FEATURE:
<223> OTHER INFORMATION: Second component of adaptor for creating single
      strand DNA

<400> SEQUENCE: 3
gcatgcgtca gatgctctcg gcagtcctga gtagcga                               37

<210> SEQ ID NO 4
<211> LENGTH: 18
<212> TYPE: DNA
<213> ORGANISM: Artificial Sequence
<220> FEATURE:
<223> OTHER INFORMATION: Primer # 1, designed for confirming adaptor
      ligation

<400> SEQUENCE: 4
tcgctactca ggactgcc                                                    18

<210> SEQ ID NO 5
```

```
<211> LENGTH: 19
<212> TYPE: DNA
<213> ORGANISM: Artificial Sequence
<220> FEATURE:
<223> OTHER INFORMATION: Primer # 2, designed for confirming adaptor
      ligation

<400> SEQUENCE: 5
gcactggtaa caacgcagg                                                    19

<210> SEQ ID NO 6
<211> LENGTH: 18
<212> TYPE: DNA
<213> ORGANISM: Artificial Sequence
<220> FEATURE:
<223> OTHER INFORMATION: Poly-a tail

<400> SEQUENCE: 6
aaaaaaaaaa aaaaaaaa                                                     18

<210> SEQ ID NO 7
<211> LENGTH: 18
<212> TYPE: DNA
<213> ORGANISM: Artificial Sequence
<220> FEATURE:
<223> OTHER INFORMATION: Complement of poly-a tail

<400> SEQUENCE: 7
tttttttttt tttttttt                                                     18

<210> SEQ ID NO 8
<211> LENGTH: 20
<212> TYPE: DNA
<213> ORGANISM: Artificial Sequence
<220> FEATURE:
<223> OTHER INFORMATION: Portion of Seq. Id. No. 1, designated as COM1

<400> SEQUENCE: 8
gcactggtaa caacgcagag                                                   20

<210> SEQ ID NO 9
<211> LENGTH: 15
<212> TYPE: DNA
<213> ORGANISM: Artificial Sequence
<220> FEATURE:
<223> OTHER INFORMATION: Portion of Seq. Id. No. 3 designated as COM2

<400> SEQUENCE: 9
cgtagactgc gtacg                                                        15

<210> SEQ ID NO 10
<211> LENGTH: 22
<212> TYPE: DNA
<213> ORGANISM: Artificial Sequence
<220> FEATURE:
<223> OTHER INFORMATION: Portion of Seq. Id. No. 3 designated as COM3

<400> SEQUENCE: 10
agcgatgagt cctgacggct ct                                                22

<210> SEQ ID NO 11
<211> LENGTH: 15
<212> TYPE: DNA
<213> ORGANISM: Artificial Sequence
<220> FEATURE:
<223> OTHER INFORMATION: Portion of Seq. Id. No. 2 designated as COM4
```

-continued

```
<400> SEQUENCE: 11
cgtacgcagt ctacg                                                       15

<210> SEQ ID NO 12
<211> LENGTH: 4
<212> TYPE: DNA
<213> ORGANISM: Artificial Sequence
<220> FEATURE:
<223> OTHER INFORMATION: Sequence designated Nn2
<221> NAME/KEY: misc_feature
<222> LOCATION: (1)..(4)
<223> OTHER INFORMATION: N is any nucleotide

<400> SEQUENCE: 12 nnnn                                                                    4

<210> SEQ ID NO 13
<211> LENGTH: 9
<212> TYPE: DNA
<213> ORGANISM: Artificial Sequence
<220> FEATURE:
<223> OTHER INFORMATION: Portion of Seq. Id. No. 2 designated as Zm
<221> NAME/KEY: misc_feature
<222> LOCATION: (1)..(9)
<223> OTHER INFORMATION: W is deoxyinosine

<400> SEQUENCE: 13 wwwwwwwww                                                               9

<210> SEQ ID NO 14
<211> LENGTH: 53
<212> TYPE: DNA
<213> ORGANISM: Artificial Sequence
<220> FEATURE:
<223> OTHER INFORMATION: Sequence ID No 1, with addition of poly-n chain
<221> NAME/KEY: misc_feature
<222> LOCATION: (39)..(39)
<223> OTHER INFORMATION: V is a nucleotide selected form the group
      consisting of A, G, and C
<221> NAME/KEY: misc_feature
<222> LOCATION: (40)..(53)
<223> OTHER INFORMATION: N is any nucleotide

<400> SEQUENCE: 14
gcactggtaa caacgcagga tttttttttt ttttttttvn nnnnnnnnnn nnn             53

<210> SEQ ID NO 15
<211> LENGTH: 90
<212> TYPE: DNA
<213> ORGANISM: Artificial Sequence
<220> FEATURE:
<223> OTHER INFORMATION: Generated single strand
<221> NAME/KEY: misc_feature
<222> LOCATION: (39)..(39)
<223> OTHER INFORMATION: V is a nucleotide selected from thr goup
      consisting of A, G, and C
<221> NAME/KEY: misc_feature
<222> LOCATION: (40)..(53)
<223> OTHER INFORMATION: N is any nucleotide

<400> SEQUENCE: 15
gcactggtaa caacgcagga tttttttttt ttttttttvn nnnnnnnnnn nnngcatgcg      60
tcagatgctc tcggcagtcc tgagtagcga                                       90

<210> SEQ ID NO 16
<211> LENGTH: 33
<212> TYPE: DNA
<213> ORGANISM: Artificial Sequence
```

```
<220> FEATURE:
<223> OTHER INFORMATION: Complement of poly-a tail with Nn2 feature
<221> NAME/KEY: misc_feature
<222> LOCATION: (19)..(19)
<223> OTHER INFORMATION: V is a nucleotide selected from he group
      consisting of A, G and C
<221> NAME/KEY: misc_feature
<222> LOCATION: (20)..(33)
<223> OTHER INFORMATION: N is any nucleotide

<400> SEQUENCE: 16
tttttttttt ttttttttvn nnnnnnnnnn nnn                              33

<210> SEQ ID NO 17
<211> LENGTH: 33
<212> TYPE: DNA
<213> ORGANISM: Artificial Sequence
<220> FEATURE:
<223> OTHER INFORMATION: Complement of Seq. Id. No. 16
<221> NAME/KEY: misc_feature
<222> LOCATION: (19)..(19)
<223> OTHER INFORMATION: V is a nucleotide selected from the group A, G
      and C
<221> NAME/KEY: misc_feature
<222> LOCATION: (20)..(33)
<223> OTHER INFORMATION: N is any nucleotide

<400> SEQUENCE: 17
aaaaaaaaaa aaaaaaaavn nnnnnnnnnn nnn                              33

<210> SEQ ID NO 18
<211> LENGTH: 90
<212> TYPE: DNA
<213> ORGANISM: Artificial Sequence
<220> FEATURE:
<223> OTHER INFORMATION: Complement of Seq. Id. No. 15
<221> NAME/KEY: misc_feature
<222> LOCATION: (39)..(39)
<223> OTHER INFORMATION: V is a nucleotide selected from the group of A,
      G and C
<221> NAME/KEY: misc_feature
<222> LOCATION: (40)..(53)
<223> OTHER INFORMATION: N is any nucleotide

<400> SEQUENCE: 18
cgtgtccatt gttgcgtcct aaaaaaaaaa aaaaaaavn nnnnnnnnn nnncgtacgc   60 agtctacgag accggtcagg actcatcgct                                  90

<210> SEQ ID NO 19
<211> LENGTH: 1
<212> TYPE: DNA
<213> ORGANISM: Artificial Sequence
<220> FEATURE:
<223> OTHER INFORMATION: Portion of Sequence Id. No. 1, identified as
      Vn1
<221> NAME/KEY: misc_feature
<222> LOCATION: (1)..(1)
<223> OTHER INFORMATION: V is a nucleotide selected from the group of A,
      G, and C

<400> SEQUENCE: 19 v                                                                  1
```